(12) United States Patent
Lesso et al.

(10) Patent No.: US 11,609,977 B2
(45) Date of Patent: Mar. 21, 2023

(54) BIOMETRIC PROCESSES, APPARATUS AND MACHINE-READABLE MEDIUMS

(71) Applicant: Cirrus Logic International Semiconductor Ltd., Edinburgh (GB)

(72) Inventors: John Paul Lesso, Edinburgh (GB); William E. Sherwood, Austin, TX (US); Patrick Bardsley, Austin, TX (US); Khaled Lakhdhar, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 264 days.

(21) Appl. No.: 16/822,885

(22) Filed: Mar. 18, 2020

(65) Prior Publication Data
US 2020/0302042 A1 Sep. 24, 2020

Related U.S. Application Data

(60) Provisional application No. 62/820,384, filed on Mar. 19, 2019.

(30) Foreign Application Priority Data

Apr. 23, 2019 (GB) ..................... 1905638

(51) Int. Cl.
*G06F 21/32* (2013.01)
*G06F 17/18* (2006.01)

(52) U.S. Cl.
CPC ............. *G06F 21/32* (2013.01); *G06F 17/18* (2013.01)

(58) Field of Classification Search
CPC . G06F 21/32; G06F 17/18; A61B 5/12; A61B 5/6803; A61B 5/6815; A61B 5/1171; G06K 9/6289; G06V 40/70
See application file for complete search history.

(56) References Cited

U.S. PATENT DOCUMENTS 9,430,629 B1* 8/2016 Ziraknejad ............ G06F 16/583
10,460,095 B2* 10/2019 Boesen ................ H04R 1/1041
(Continued)

OTHER PUBLICATIONS

Combined Search and Examination Report under Sections 17 and 18(3), UKIPO, Application No. GB1905638.1, dated Oct. 18, 2019.
(Continued)

*Primary Examiner* — Meng Li
(74) *Attorney, Agent, or Firm* — Jackson Walker L.L.P.

(57) ABSTRACT

A biometric processor comprises: one or more inputs configured to receive first ear biometric data acquired in respect of a first ear of a user and second ear biometric data acquired in respect of a second ear of the user; a processing module configured to perform a biometric algorithm on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores; a fusion module configured to apply first and second weights to the respective first and second biometric scores to obtain first and second weighted biometric scores, and to combine at least the first and second weighted biometric scores to generate an overall biometric score, wherein the first and second weights are different to each other; and wherein a biometric result is based on the overall biometric score.

21 Claims, 9 Drawing Sheets

(56) References Cited

U.S. PATENT DOCUMENTS

| | | | |
|---|---|---|---|
| 2015/0028996 A1* | 1/2015 | Agrafioti | G06F 21/40 |
| | | | 340/5.82 |
| 2018/0082304 A1* | 3/2018 | Summerlin | G06Q 20/3229 |
| 2019/0005217 A1* | 1/2019 | Kim | G06K 9/6269 |
| 2019/0012445 A1 | 1/2019 | Lesso et al. | |
| 2019/0012448 A1 | 1/2019 | Lesso | |
| 2019/0044969 A1* | 2/2019 | Pilkington | H04L 63/1433 |

OTHER PUBLICATIONS

Akkermans, T.H. et al., "Acoustic Far Recognition", International Conference on Biometrics, pp. 697-705, Springer, 2006.
Vora, A. et al., "Review on Fusion Algorithms for Multimodal Authentication System", IJEDR, vol. 3(2), pp. 911-917, 2015.
Yasuhara, Masaki et al., "Feature Selection and Its Evaluation in Binaural Ear Acoustic Authentication", Audio Engineering Society, Ireland, Mar. 2019.

* cited by examiner

BIOMETRIC PROCESSES, APPARATUS AND MACHINE-READABLE MEDIUMS

TECHNICAL FIELD

Embodiments of the disclosure relate to biometric processes, apparatus and machine-readable mediums, and particularly to processes, apparatus and machine-readable mediums utilizing ear biometric data.

BACKGROUND

It is known that the acoustic properties of a user's ear, whether the outer parts (known as the pinna or auricle), the ear canal or both, differ substantially between individuals and can therefore be used as a biometric to identify the user. One or more loudspeakers or similar transducers positioned close to or within the ear generate a stimulus, and one or more microphones similarly positioned close to or within the ear detect the response of the ear to the stimulus. One or more features may be extracted from the response signal, and used to characterize an individual.

For example, the ear canal is a resonant system, and therefore one feature which may be extracted from the response signal is the resonant frequency of the ear canal. If the measured resonant frequency (i.e. in the response signal) differs from a stored resonant frequency for the user, a biometric algorithm coupled to receive and analyse the response signal may return a negative result. Other features extracted from the response signal may comprise one or more mel frequency cepstrum coefficients. More generally, the transfer function between the stimulus and the measured response signal (or features of the transfer function) may be determined, and compared to a stored transfer function (or stored features of the transfer function) which is characteristic of the user.

Other acoustic properties of a user's ear include otoacoustic emissions, whether spontaneous (i.e., generated by the ear without external stimulation) or evoked (i.e., generated by the ear in response to a stimulus signal such as one or more pure tones, a tone burst, etc). Such otoacoustic emissions may also differ between individuals and can therefore be used to discriminate between individuals or to identify a particular individual.

Thus input biometric data is acquired from a user and compared to a stored biometric profile associated with an authorised user. A biometric score is derived based on the comparison, indicative of the similarity between the acquired biometric data and the stored profile. In certain arrangements, the input biometric data may be compared to both the stored biometric profile and one or more cohorts of biometric profiles corresponding to the public at large. In this case, the biometric score is indicative of the likelihood that the input biometric data corresponds to the stored biometric profile as opposed to a member of the general public. The biometric score may then be compared to a threshold to determine whether the user should be authenticated as the authorised user or not.

One problem faced by biometric algorithms is the need to achieve acceptable performance in two respects. First, the algorithm should provide acceptable security so that unauthorised users are not falsely recognized as authorised users. The likelihood that the algorithm will accept an access attempt by an unauthorised user is known as the false acceptance rate (FAR), and should be kept low if the algorithm is to provide reasonable security. Second, the algorithm should work reliably, so that authorised users are not falsely rejected as unauthorised. For example, the biometric data for a user will typically vary to a limited extent between access attempts. This may be due to various factors, such as a changing environment (and thus different noise levels), different positioning of the biometric data acquisition system (e.g., an earbud which is inserted at a different distance into the ear), etc. The likelihood that the algorithm will reject an access attempt by an authorised user is known as the false rejection rate (FRR), and should also be kept low if the algorithm is not to prove frustrating for authorised users seeking authentication.

The problem is that these two performance requirements are inter-dependent. A low FRR can be achieved by relaxing the requirements for a user to achieve authentication (e.g. lowering the threshold). However, this will also have the consequence of increasing the FAR. Conversely, a low FAR can be achieved by making the requirements for a user to achieve authentication stricter (e.g., increasing the threshold). However, this will have the consequence of increasing the FRR.

FIG. 1 is a schematic graph showing the approximate variation of FAR and FRR with changing threshold, for a biometric score which varies between 0 (zero correspondence between the input biometric data and the stored biometric profile) and 1 (exact correspondence between the input biometric data and the stored biometric profile). At very low values of the threshold (i.e., close to 0), the FAR is high and the FRR is low, as the level of similarity between the input biometric data and the stored biometric profile required for a "match" is relatively low. Conversely, at very high values of the threshold (i.e., close to 1), the FAR is low and the FRR is high, as the level of similarity between the input biometric data and the stored biometric profile required for a "match" is relatively high.

That said, it is possible to decrease both the FAR and FRR, increasing the efficacy of the biometric process overall. For example, the biometric algorithm may be carefully designed to measure the similarity between the acquired data and the stored profile with a higher level of confidence. However, designing the algorithm to achieve high performance is difficult.

Alternatively or additionally, the biometric data itself may be chosen to increase the efficacy of the process. For example, the quality of the biometric data (e.g., noise levels, quantization errors, etc) will affect the ability of the biometric process to discriminate between users accurately. In addition, different biometric data may have different discriminatory ability. That is, biometric data which is similar to that of other users has relatively low discriminatory ability; conversely, biometric data which is different to that of other users has relatively high discriminatory ability and may perform better when used in a biometric process. As a simple example, the biological sex of a user has low discriminatory ability, as it is the same for approximately half the population; a fingerprint has much higher discriminatory ability as it differs significantly between individuals. Thus the type of biometric data affects the efficacy of the biometric process.

This efficacy of the biometric process may be quantified using the equal error rate (EER). As noted above, the FAR and FRR can be changed by varying the threshold with which the biometric score is compared. The FAR and FRR generally change in opposite directions with variation of the threshold, and therefore there is a threshold value at which the FAR and FRR are equal to each other. The EER is the error rate at this threshold value. The lower the EER, the more effective the biometric process.

It is a long-standing goal for those skilled in the art of biometrics to increase the efficacy of biometric processes. Embodiments of the present disclosure seek to address this and other problems.

SUMMARY

According to one aspect of the disclosure, there is provided a biometric processor, comprising: one or more inputs configured to receive first ear biometric data acquired in respect of a first ear of a user and second ear biometric data acquired in respect of a second ear of the user; a processing module configured to perform a biometric algorithm on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores; a fusion module configured to apply first and second weights to the respective first and second biometric scores to obtain first and second weighted biometric scores, and to combine at least the first and second weighted biometric scores to generate an overall biometric score, wherein the first and second weights are different to each other; and wherein a biometric result is based on the overall biometric score.

Further aspects provide electronic apparatus comprising such a biometric processor. In an alternative embodiment, there is provided an electronic apparatus comprising processing circuitry and a non-transitory machine-readable medium storing instructions which, when executed by the processing circuitry, cause the processing circuitry to: obtain first ear biometric data acquired in respect of a first ear of a user and second ear biometric data acquired in respect of a second ear of the user; perform a biometric algorithm on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores; apply first and second weights to the respective first and second biometric scores to obtain first and second weighted biometric scores, and combine at least the first and second weighted biometric scores to generate an overall biometric score, wherein the first and second weights are different to each other; and generate a biometric result based on the overall biometric score.

In another aspect, a method is provided of performing a biometric process. The method comprises: obtaining first ear biometric data acquired in respect of a first ear of a user and second ear biometric data acquired in respect of a second ear of the user; performing a biometric algorithm on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores; applying first and second weights to the respective first and second biometric scores to obtain first and second weighted biometric scores, and combining at least the first and second weighted biometric scores to generate an overall biometric score, wherein the first and second weights are different to each other; and generating a biometric result based on the overall biometric score.

A further aspect of the disclosure provides a biometric processor, comprising: one or more inputs configured to receive first ear biometric data acquired in respect of a first ear of a user and second ear biometric data acquired in respect of a second ear of the user; a processing module configured to perform one or more biometric algorithms on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores; and a fusion module configured to combine at least the first and second biometric scores to generate an overall biometric score. The first and second biometric scores are combined in a polynomial transform of the form $$\sum_{i=0}^{p} \sum_{j=0}^{q} \alpha_{ij} S_L^i S_R^j$$

where p and q denote degrees of the polynomial in the first and second biometric scores respectively, and where $S_L$ and $S_R$ are the first and second biometric scores respectively. The polynomial transform is input to a nonlinear function to generate the overall biometric score. A biometric result is based on the overall biometric score.

BRIEF DESCRIPTION OF THE DRAWINGS

For a better understanding of examples of the present disclosure, and to show more clearly how the examples may be carried into effect, reference will now be made, by way of example only, to the following drawings in which.

DETAILED DESCRIPTION

One known technique for improving the efficacy of the biometric process is to combine (or "fuse") multiple authentication processes together, whether biometric or not. In the context of ear biometrics, for example, ear biometric processes for the left and right ears may be fused.

Score-level fusion or decision-level fusion may be used. In the former case, separate biometric scores are calculated for left and right ears (based on separate stored profiles for the left and right ears), and then combined to form an overall biometric score. That overall biometric score is then compared to a threshold to generate a decision as to whether the user is an authorised user or not. In the latter case, separate biometric scores are again calculated for left and right ears, but these scores are individually compared to one or more thresholds to generate respective decisions for each of the left and right ears. The decisions are then fused to authenticate the user as an authorised user. In one simple example, both decisions must be positive to authenticate the user.

Embodiments of the present disclosure are concerned with score-level fusion of ear biometric data for left and right ears.

The improvement given by the fusion of left and right ear biometrics depends on how correlated the left and right ears of a given user are. The higher the correlation between two ears for a given user, the less improvement the fusion will provide. This can be intuitively understood by considering that highly correlated ears will have the same shape. Thus repeating the same process for left and right ears and fusing the scores will not provide a particular advantage.

Figure 1:
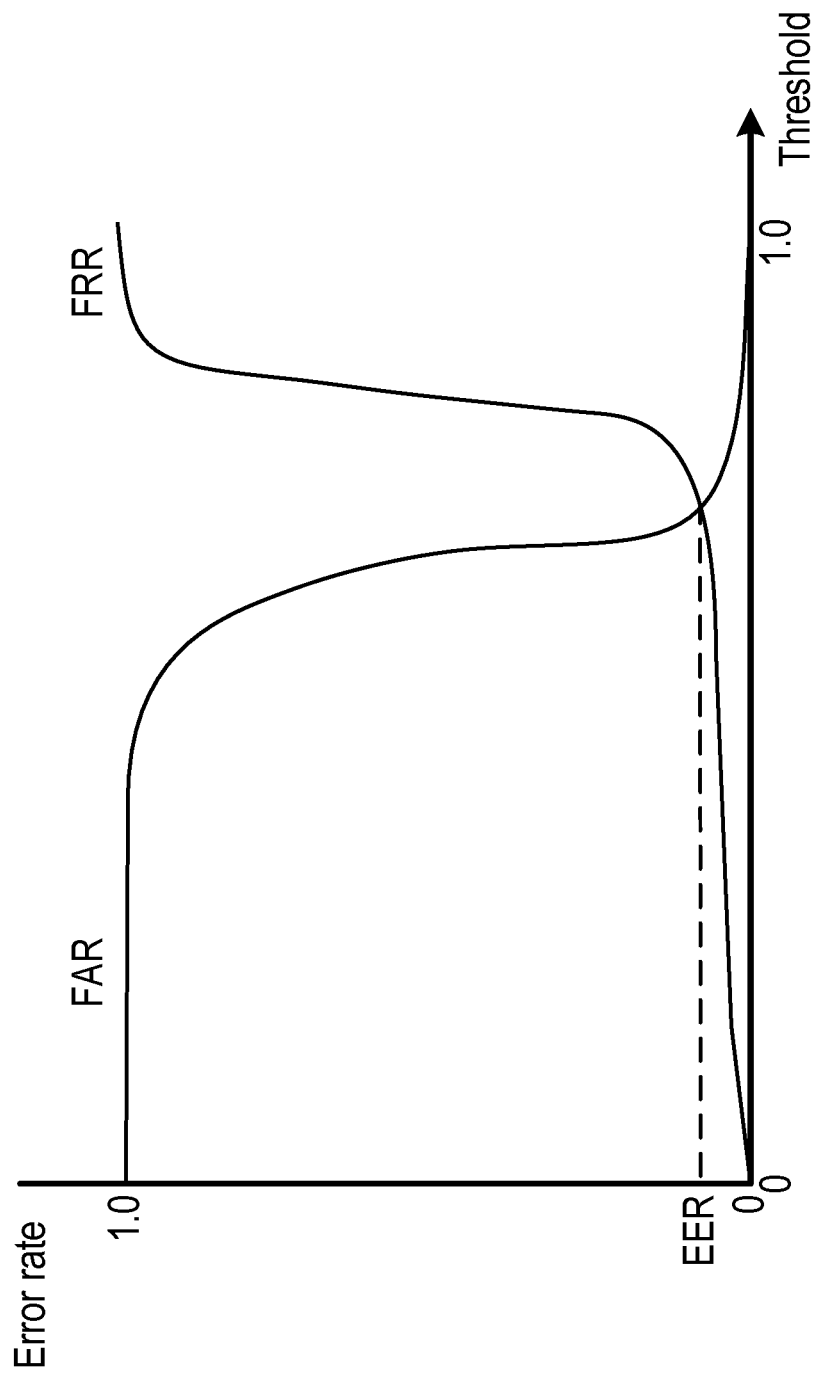
FIG. 1 shows the variation of error rates in a biometric system.
Figure 2:
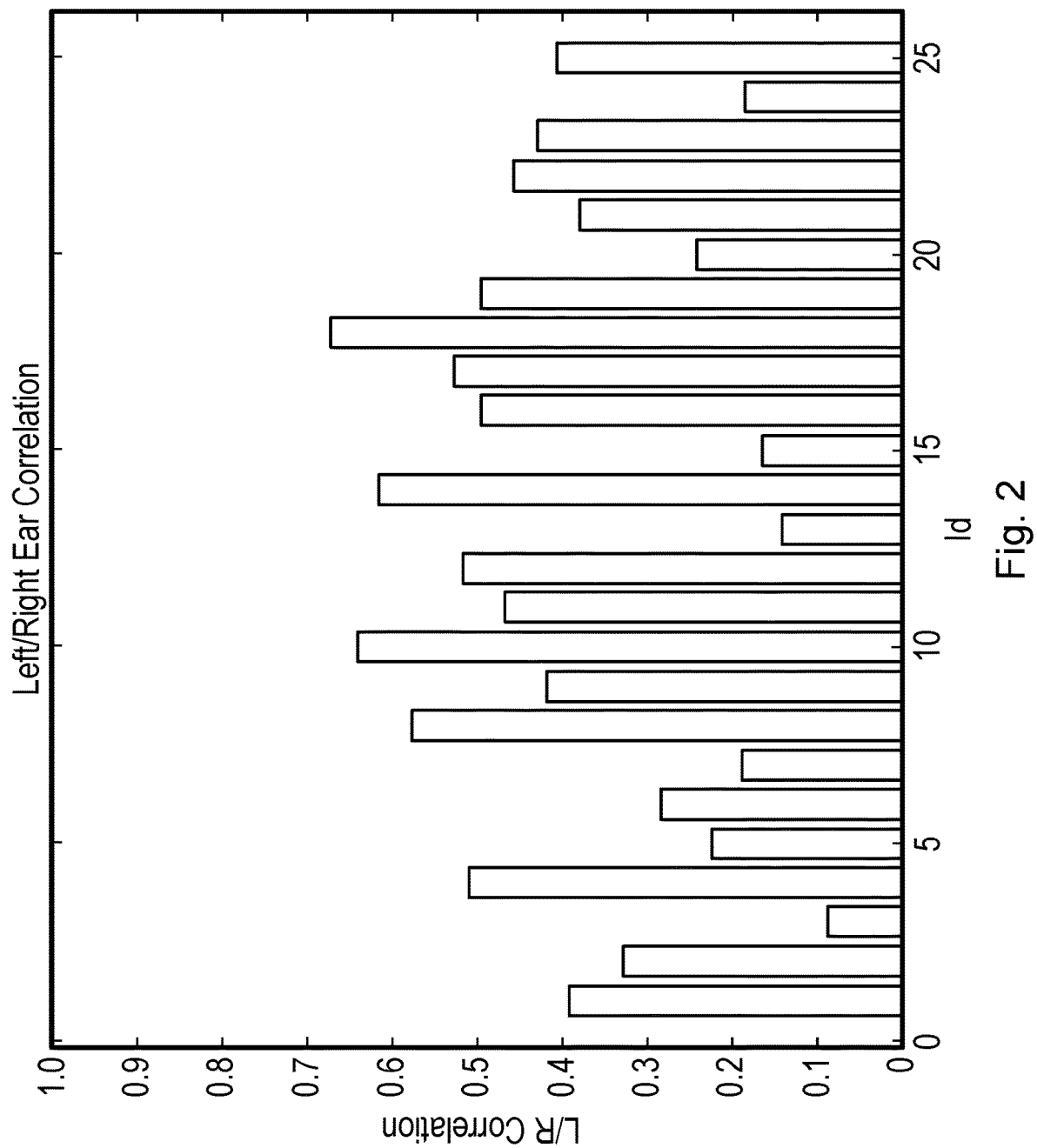
FIG. 2 shows the correlation between left and right ear biometric data for a series of users.

FIG. 2 is a bar chart showing the correlation coefficient between left and right ear biometric data for a series of 25 sample users, where the correlation coefficient varies between 0 (indicating a complete lack of correlation) and 1 (indicating exact correlation). It can be seen that the left and right ear biometric data is highly correlated for some users (e.g., particularly users 10, 14 and 18), and relatively uncorrelated for other users (e.g., particularly users 3, 13 and 15).

This variable degree of correlation suggests that for some users there may be a substantial advantage to fusing biometric data for separate ears to improve scores.

An additional consideration is that the different ears may themselves have different discriminative properties. That is, biometric data for the left ear may be more discriminative than biometric data for the right ear, or vice versa. In this context, the discriminative ability of the biometric corresponds to the ability for that biometric data to discriminate from the general public (e.g., as defined by one or more cohorts).

Figure 3:
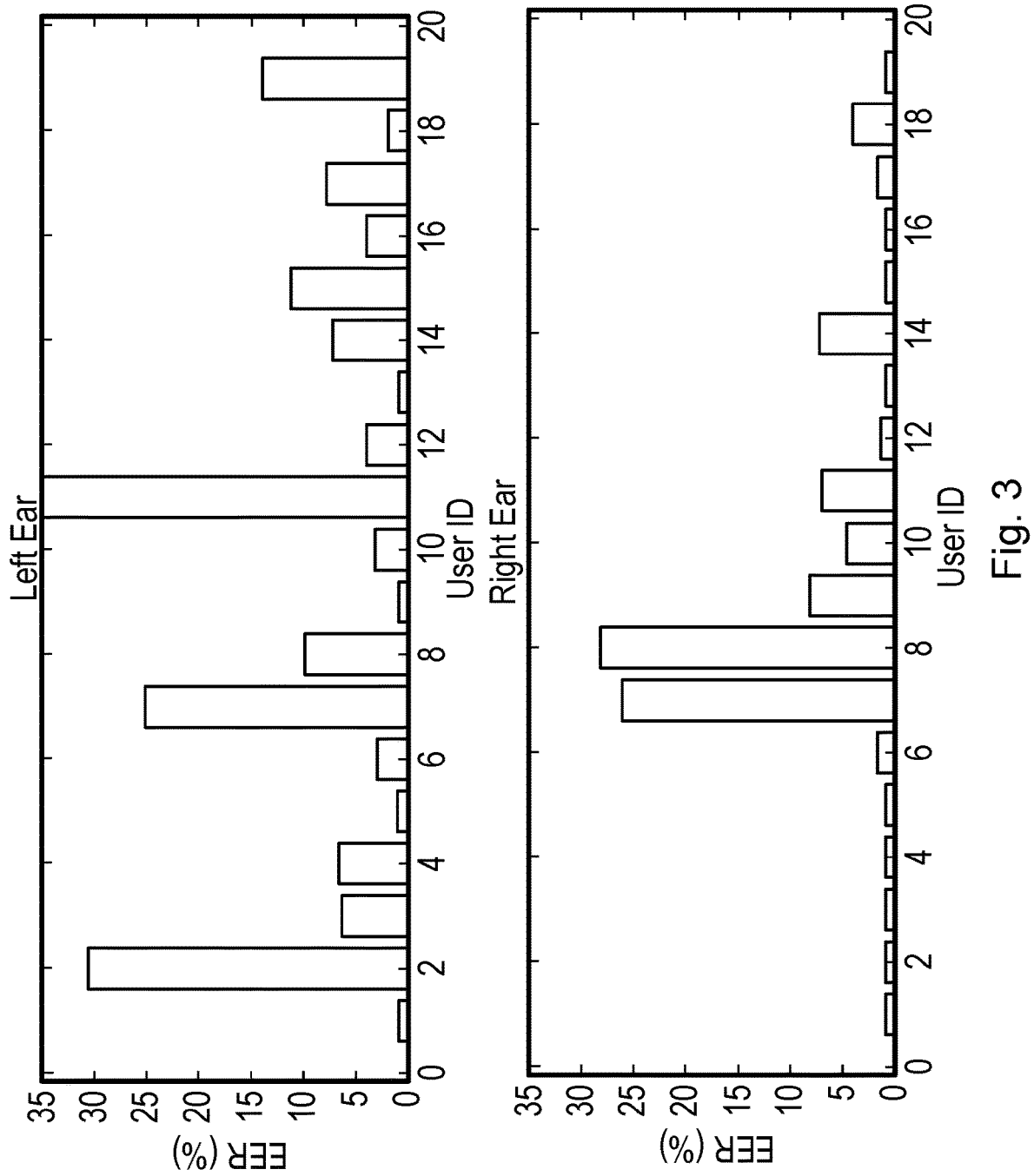
FIG. 3 shows the equal error rate for the left and right ears of a series of users.

For example, FIG. 3 shows bar charts of the equal error rate (EER) for the left and right ears of a series of users. The user ID is constant between each bar chart. Thus, the particular user ID in the bar charts for the left and right ears correspond to the same user. It will be recalled from the discussion above that the EER is an indicator of how discriminative biometric data is. The lower the EER, the more discriminative the biometric data.

It can be seen that there is a surprisingly wide range of EER between different ears. Different users have more or less discriminative ears. Further, a particular user's left ear may be more discriminative than their right (or vice versa). For example, user 2 has a discriminative left ear, but a right ear which is not discriminative. User 11 has a left discriminative left ear, but a less discriminative right ear. This can be due to a number of factors, such as differences in ear shape, other physiological differences, how the user operates the biometric data acquisition system (e.g., a better fit when using their dominant hand). The quality of the stored template or profile (acquired during a process known as enrolment) may also play a part.

Embodiments of the present disclosure take advantage of this difference in discriminative properties when fusing biometric processes for the left and right ears of a user. In particular, the discriminative properties of the biometric data are used to weight biometric scores for the left and right ears, so as to emphasize the biometric score for the more-discriminative ear. In this way, the efficacy of the overall process (e.g., as indicated by the EER) can be expected to improve.

To fuse the biometric scores associated with the left and right ears, the biometric scores for the left ear $s_L$ and the right ear $s_R$ may be combined as follows:

$$s = w_L s_L + w_R s_R$$

where s is the overall biometric score and $w_L$ and $w_R$ are weights for the left and right ears respectively. In this example the weights are normalized such that $w_L+w_R=1$. If the weights do not sum to 1, a normalization factor may be applied to the equation (e.g., by dividing the weighted sum by the sum of the weights).

The weights may be configured so as to emphasize the biometric score for the biometric data which is more discriminative. Thus, where the biometric properties of the left ear are more discriminative than the right ear, the weight for the left ear $w_L$ is configured to be greater than the weight for the right ear $w_R$ (and vice versa).

One way of achieving this is to configure the weights as a function of the EER for the respective ear. For example:

$$w_L = \frac{EER_R}{EER_L + EER_R}$$

$$w_R = \frac{EER_L}{EER_L + EER_R}$$

where $EER_L$ is the EER associated with the left ear, and $EER_R$ is the EER associated with the right ear.

Here it will be recalled that the lower the EER, the more discriminative the biometric data. Thus in this example, the weights for each ear are configured inversely proportional to the EER for the respective ear.

In another example, the weights may be configured so as to optimize the false rejection rate or the false acceptance rate. Here the weights may be configured proportionally to the respective false rejection rate or false acceptance rate. In one example, which depends on the false rejection rate, the weights may be configured as follows:

$$w_L = \frac{FRR_L}{FRR_L + FRR_R}$$

$$w_R = \frac{FRR_R}{FRR_L + FRR_R}$$

where $FRR_L$ is the FRR associated with the left ear, and $FRR_R$ is the FRR associated with the right ear.

In another example, which depends on the false acceptance rate, the weights may be configured as follows:

$$w_L = \frac{FAR_L}{FAR_L + FAR_R}$$

$$w_R = \frac{FAR_R}{FAR_L + FAR_R}$$

where $FAR_L$ is the FAR associated with the left ear, and $FAR_R$ is the FAR associated with the right ear.

In another embodiment of the present disclosure, left and right ear biometric scores, $S_L$ and $S_R$, may be combined into a single overall score $S_F$ via a composite function $h(S_R,S_L)$ comprising (a) a linear affine transform of $S_L$ and $S_R$, $g(S_R,S_L)$, followed by (b) a sigmoid (logistic) function:

$$S_F = h(S_R, S_L) = \frac{1}{1 + e^{-g(S_R,S_L)}} = \frac{1}{1 + e^{-(\alpha_0 + \alpha_R S_R + \alpha_L S_L)}} \quad (1)$$

$h(S_R,S_L)$ is a nonlinear function whose output lies in the range [0,1] (note that in this embodiment $S_L$ and $S_R$ are not required to be non-negative). A useful property of this embodiment is that $S_F=h(S_R,S_L)$ may be interpreted as the conditional probability that the subject is the authorized ("target") user, given the subject's right and left ear biometric scores $S_R$, $S_L$. Writing y=1 if the subject is in fact the target user, and y=0 otherwise, then $$S_F = h(S_R, S_L) = \frac{1}{1 + e^{-g(S_R,S_L)}} = P(y=1 \mid S_R, S_L) \quad (2)$$

Thus deciding to accept a user's authentication attempt only if the conditional probability of the user being genuine is sufficiently high simply requires checking whether the overall score $S_F$ is greater than a threshold T. The threshold T may be chosen to satisfy operational requirements for FAR and/or FRR.

Those skilled in the art will appreciate that alternative functions may be used than the sigmoid function. For example, double sigmoid and tanh (hyperbolic tangent) functions are also suitable.

In this embodiment the relative discriminative value of left versus right ear biometric scores is captured by the shape of the function $h(S_R,S_L)$ and is reflected in the slope of $h(S_R,S_L)$ with respect to $S_R$ or $S_L$ at any given point. A steeper slope indicates higher discriminative value.

The coefficients $\alpha_0,\alpha_R,\alpha_L$ of the linear affine transform $g(S_R,S_L)=\alpha_0+\alpha_R S_R+\alpha_L S_L$ are constants whose values are determined by minimizing a cost function $J(h,\alpha_0,\alpha_R,\alpha_L)$ over a training set of example right and left ear biometric score pairs $(S_R^{(i)},S_L^{(i)})$. This training set may be derived from measurements of the left and right acoustic ear biometric features, obtained from multiple subjects, which have been scored by left and right ear biometric processors. An example of a cost function $J(h,\alpha_0,a_R,\alpha_L)$ whose minimization optimizes the values of the coefficients $\alpha_0,\alpha_R,\alpha_L$ is the log-likelihood cost function $$J(h, \alpha_0, \alpha_R, \alpha_L) = \\ -\frac{1}{m}\sum_{i=1}^{m}\left[y^{(i)}\log(h(S_R^{(i)}, S_L^{(i)})) + (1-y^{(i)})(1-\log(h(S_R^{(i)}, S_L^{(i)})))\right] + \beta(\alpha_R^2 + \alpha_L^2) \quad (3)$$

Here m is the number of training examples, $\beta \geq 0$ is a constant regularization parameter (which may be adjusted to improve the speed or robustness of the optimization procedure), and $y^{(i)}=1$ if the ith training example belongs to the target (authorized user) class and 0 otherwise. Those skilled in the art will appreciate that alternative cost functions may be used without departing from the scope of the claims appended hereto.

Gradient descent is one example of an efficient iterative procedure which will minimize a cost function $J(h,\alpha_0,\alpha_R,\alpha_L)$ as in (3) to produce optimal values of the coefficients $\alpha_0,\alpha_R,\alpha_L$. Those skilled in the art will appreciate that other optimization procedures may also be used with similar effectiveness.

Figure 4:
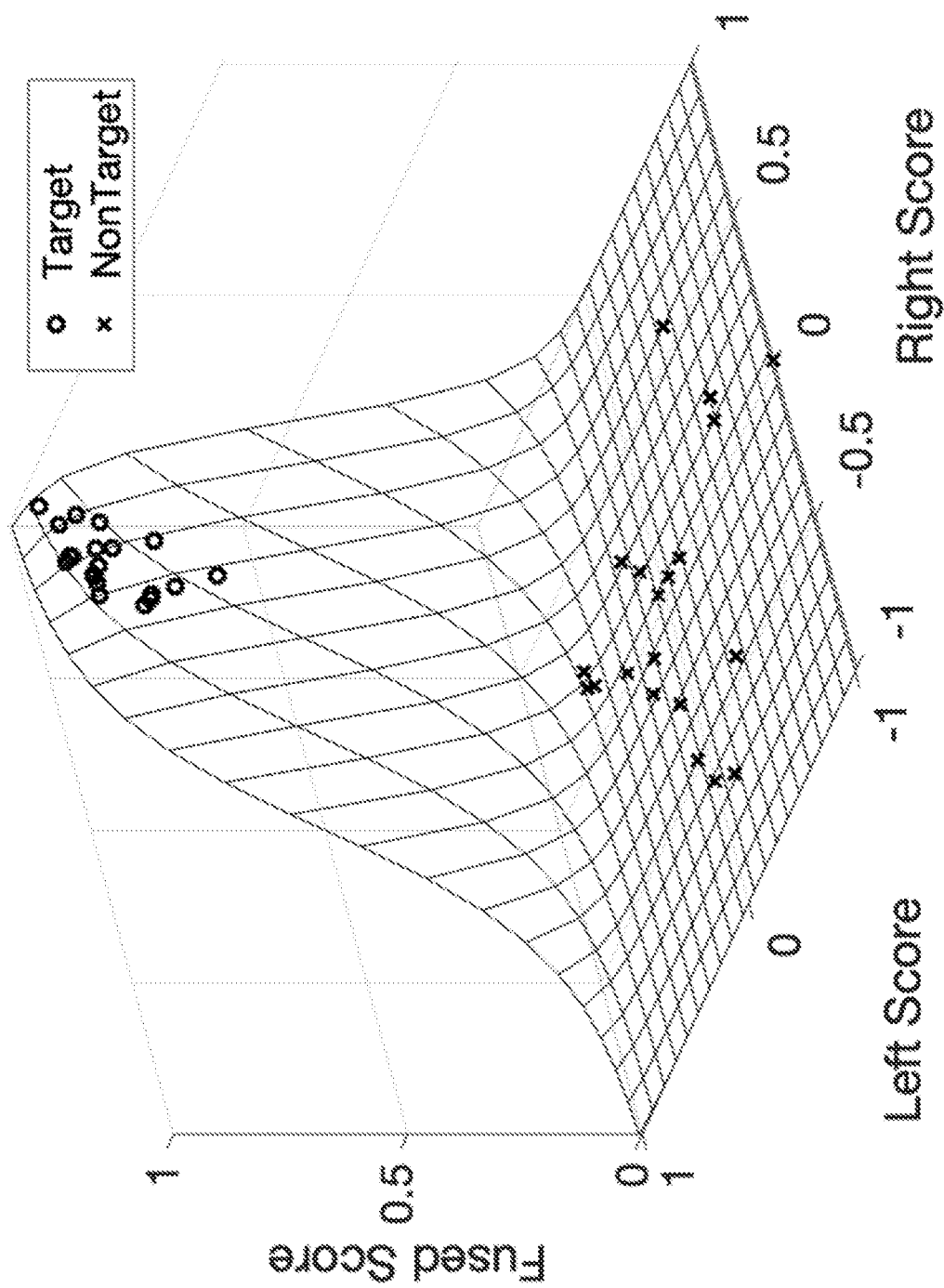
FIGS. 4, 5, and 6 show example plots of fused biometric scores derived from individual biometric scores for the left and right ears of user.
Figure 5:
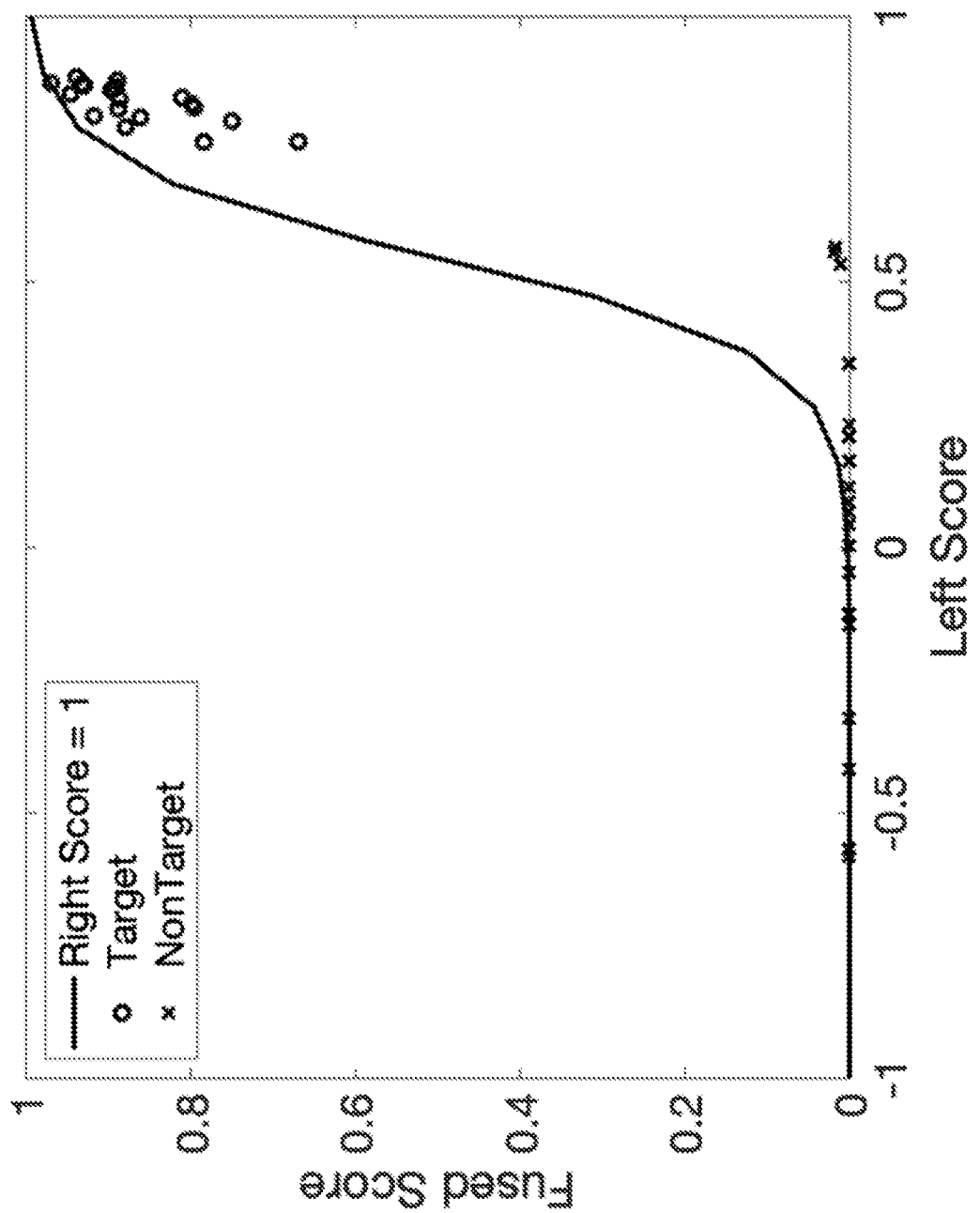
Figure 6:
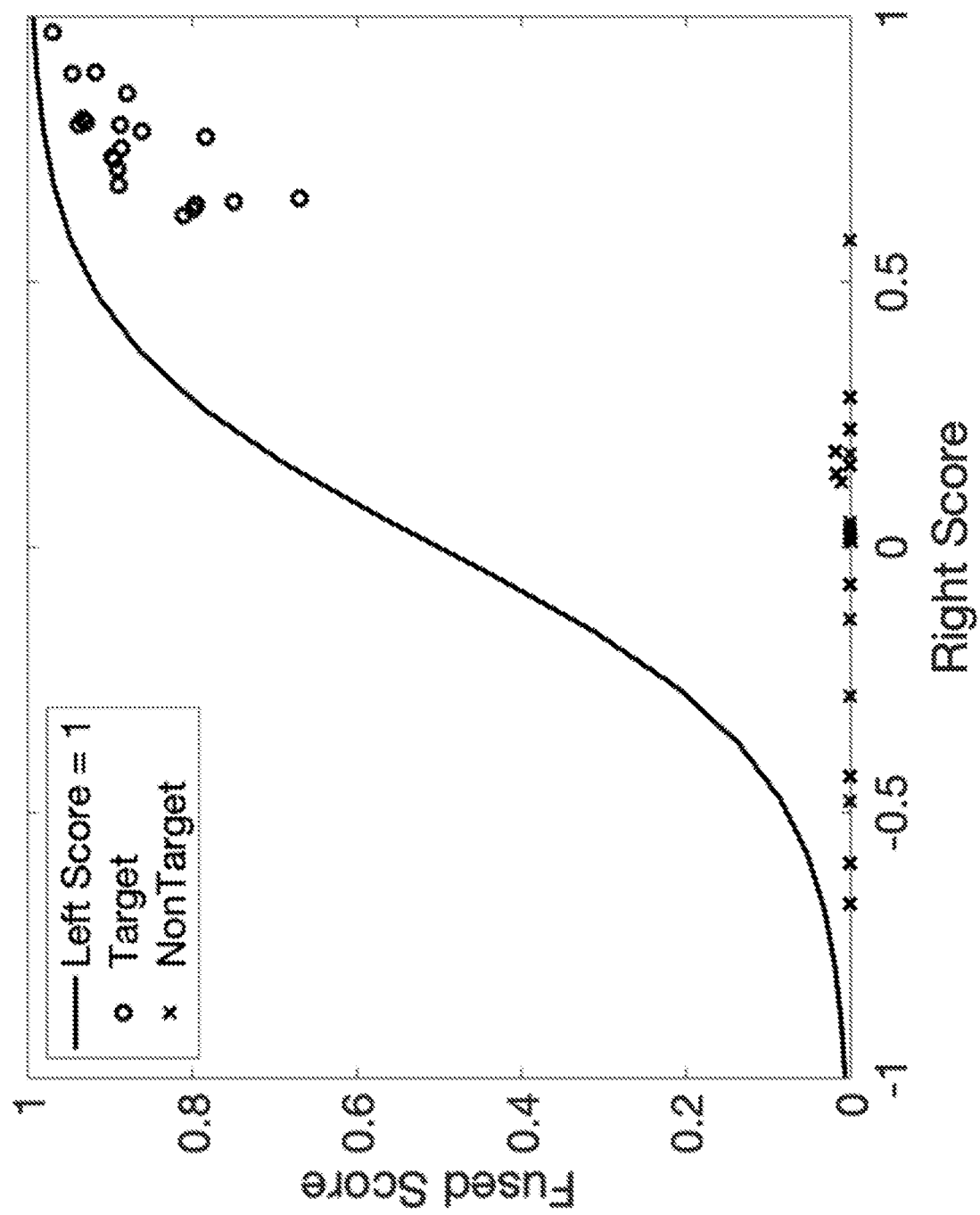

FIG. 4 shows an example plot of $h(S_R,S_L)$ as in equation (1), where the coefficients $\alpha_0,\alpha_R,\alpha_L$ were determined using gradient descent with the cost function $J(h,\alpha_0, \alpha_R,\alpha_L)$ as in equation (3). Also shown are target (genuine) and nontarget (imposter) left and right ear biometric score pairs $(S_R^{(i)},S_L^{(i)})$ used in the training set. The surface $h(S_R,S_L)$ is asymmetrical with respect to $S_R$ or $S_L$, reflecting the unequal discriminative value of left and right ear biometric scores. FIG. 5 shows a cross-section $h(S_R=1, S_L)$ along with the left ear biometric scores $S_L^{(i)}$; FIG. 6 shows a cross-section $h(S_R, S_L=1)$ along with the right ear biometric scores $S_R^{(i)}$. From the slopes of the sigmoidal cross-sections it can be inferred that, for this example data, left ear biometric scores are more discriminative than the right ear biometric scores.

In other embodiments, the linear affine transform $g(S_R,S_L)$ of step (a) may be generalized to other functional forms, such as a multivariate polynomial transform $f(S_R,S_L)$:

$$S_F = h(S_R, S_L) = \frac{1}{1+e^{-f(S_R,S_L)}} = \frac{1}{1+e^{-\left(\sum_{i=0}^{p}\sum_{j=0}^{q}\alpha_{ij}S_L^i S_R^j\right)}} \quad (4)$$

Here p and q denote the degrees of the polynomial in the left and right scores respectively. This embodiment can capture more detail of any nonlinear interdependencies between the left and right ear biometric processors' score outputs. For this embodiment the cost function $J(h,\alpha_{ij})$ may be identical to equation (3) except that the regularization term $\beta(\alpha_R^2+\alpha_L^2)$ is replaced with $\beta(\Sigma_{i=0}^p\Sigma_{j=0}^q\alpha_{ij}^2-\alpha_{00}^2)$. Optimal values for $\alpha_{ij}$ may be obtained in similar fashion by minimizing the cost function $J(h,\alpha_{ij})$.

Figure 7:
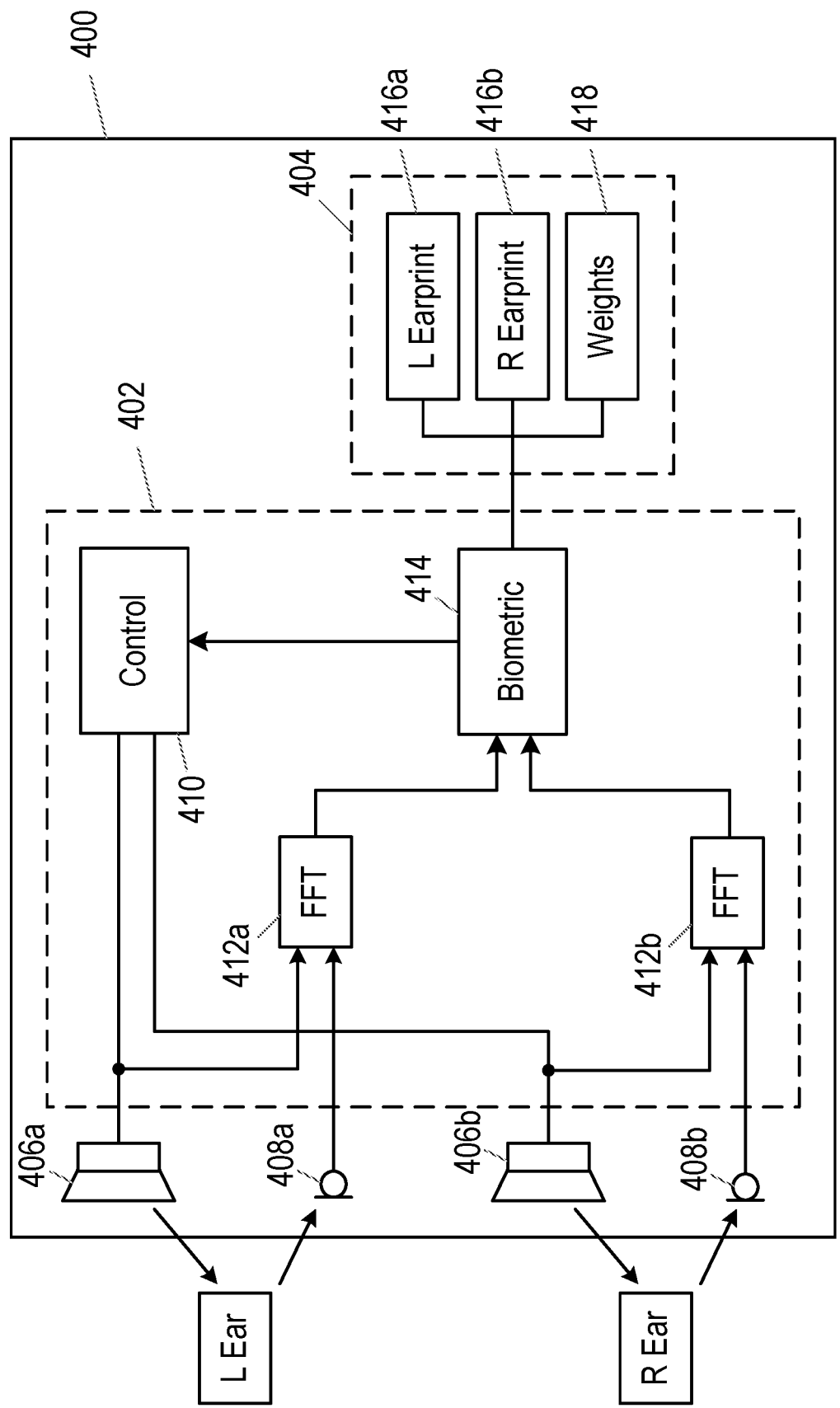
FIG. 7 is a schematic diagram of an electronic apparatus according to embodiments of the disclosure.

FIG. 7 shows an electronic apparatus 400 according to embodiments of the disclosure.

The electronic apparatus 400 comprises processing circuitry 402, which may comprise one or more processors, such as a central processing unit or an applications processor (AP), or a digital signal processor (DSP). In one embodiments, the processing circuitry 402 comprises a biometric processor.

The electronic apparatus 400 further comprises memory 404, which is communicably coupled to the processing circuitry 402. The memory 404 may store instructions which, when carried out by the processing circuitry 402, cause the processing circuitry to carry out one or more methods as described below (see the mechanism shown in FIG. 8 and the method shown in FIG. 9 for example). The processing circuitry 402 may perform methods as described herein on the basis of data and program instructions stored in memory 404. Memory 404 may be provided as a single component or as multiple components or co-integrated with at least some of processing circuitry 402. Specifically, the methods described herein can be performed in processing circuitry 402 by executing instructions that are stored in non-transient form in the memory 404, with the program instructions being stored either during manufacture of the electronic apparatus 400 or by upload while the electronic apparatus 400 is in use.

The processing circuitry 402 comprises a control module 410, which is coupled to respective loudspeakers 406*a*, 406*b* (collectively 406). The control module 410 generates one or more electrical audio signals and provides the electrical audio signal(s) to the loudspeakers 406. Those skilled in the art will appreciate that devices such as amplifiers and digital-to-analogue converters (DACs) are omitted for clarity.

The loudspeakers 406 generate corresponding acoustic signals which are output to the user's ears. The acoustic signal may be sonic or ultra-sonic, for example. The acoustic signal may have a flat frequency spectrum, or be preprocessed in such a way that those frequencies that allow for a good discrimination between individuals are emphasized (i.e. have a higher amplitude than other frequencies).

The acoustic signals may be output to all or a part of the user's ears (i.e. the auricle or the ear canal). The acoustic signals are reflected off the ears, and the reflected signals (or echo signals) are detected and received by respective microphones 408a, 408b (collectively 408). Each reflected signal thus comprises data which is characteristic of the individual's respective ears, and suitable for use as a biometric. The microphones 408 may be further configured as error microphones for a feedback active noise-cancellation (ANC) system. In this way, the acquisition of ear biometric data may not require additional hardware than would ordinarily be provided in ANC headphones or earphones. In an alternative embodiment, the microphones may not be separate devices to the loudspeakers, and instead may comprise additional sense circuitry configured around the loudspeaker to allow the loudspeaker to function as a microphone.

In the illustrated embodiment, the loudspeakers 406 and the microphones 408 are shown as part of the electronic apparatus 400. This may be the case where the electronic apparatus 400 is a headset, a pair of earphones (or earbuds), or similar device, and the processing circuitry 402 is located within the same apparatus. In alternative embodiments, the loudspeakers 406 and the microphones 408 may be provided in a separate apparatus to the processing circuitry 402. In the latter case, the loudspeakers 406 and the microphones 408 may be provided in a peripheral device such as a headset or a pair of earphones (or earbuds), whereas the processing circuitry 402 is comprised within a host device such as a smartphone, an audio player, a tablet computer, or a mobile or cellular phone.

The signals detected by the microphones 408 are in the time domain. However, the features extracted for the purposes of the biometric process may be in the frequency domain (in that it is the frequency response of the user's ear which is characteristic). The processing circuitry 402 may therefore further comprise respective Fourier transform modules 412a, 412b (collectively 412), which convert the reflected signals to the frequency domain. For example, the Fourier transform modules 412 may implement a fast Fourier transform (FFT). Those skilled in the art will further appreciate that transformation of the reflected signals for the left and right ears to the frequency domain may be performed by a single Fourier transform module which is multiplexed between the two signal paths. In some examples the biometric process may not be in the frequency domain, so any Fourier transform modules may be omitted.

The transformed signals are then passed to a biometric module 414, which may extract one or more features from the signals, and then perform a biometric process on the extracted features.

The features extracted from the signals may comprise one or more of: one or more resonant frequencies of the respective ear; one or more cepstrum coefficients (such as mel frequency cepstrum coefficients); the frequency response of the ear at one or more predetermined frequencies, or across one or more ranges of frequencies.

In some embodiments the acoustic stimuli may be tones of predetermined frequency and amplitude. In other embodiments the processing circuitry 402 may be configurable to apply music to the loudspeakers 406 (or other acoustic output which is not predetermined), e.g. normal playback operation, and the biometric module 414 may be configurable to extract the response or transfer function from whatever signal components the acoustic stimuli contain.

Thus in some embodiments the biometric module 414 may be designed with foreknowledge of the nature of the acoustic stimulus, for example knowing the spectrum of the acoustic stimulus signals, so that the response or transfer function may be appropriately normalised. In other embodiments the biometric module 414 may comprise a second input to receive the acoustic stimulus (e.g. playback music) and hence obtain information about the acoustic stimuli or their spectrum so that the transfer function between the reflected signals and the acoustic stimuli can be determined (from which may be derived the desired feature parameters). In the latter case, the stimulus signals may also pass to the biometric module 414 via the Fourier transform modules 412.

As noted above, the biometric module 414 is configured to perform a biometric process on the extracted features. For example, the biometric module 414 may perform a biometric enrolment, in which the extracted features (or parameters derived therefrom) are stored as part of biometric data which is characteristic of the individual. The biometric data may be stored within the electronic apparatus 400 (e.g., in the memory 404) or remote from the electronic apparatus 400 (and accessible securely by the biometric module 414). Such stored data may be known as a biometric profile or an "earprint". In the present context, separate ear prints are acquired in respect of each ear: an earprint 416a for the left ear; and an earprint 416b for the right ear (collectively 416).

The biometric module 414 may be further configured to calculate weights $w_L$ and $w_R$ for each ear, and to store those weights 418 (e.g., in the memory 404) for future use in fusing biometric scores as described above. The weights may be initially calculated during enrolment, and then updated during use of the electronic apparatus 400. Further detail regarding this aspect of the disclosure is provided below with respect to FIG. 9. Those skilled in the art will appreciate that the biometric module 414 may alternatively calculate and store one or more parameters indicative of the discriminatory ability of the biometric data, from which the weights can be calculated when needed.

As noted above, in another example, the biometric module 414 may perform a biometric authentication process in which features extracted from the reflected signals are compared to corresponding features in the stored ear prints 416.

Figure 8:
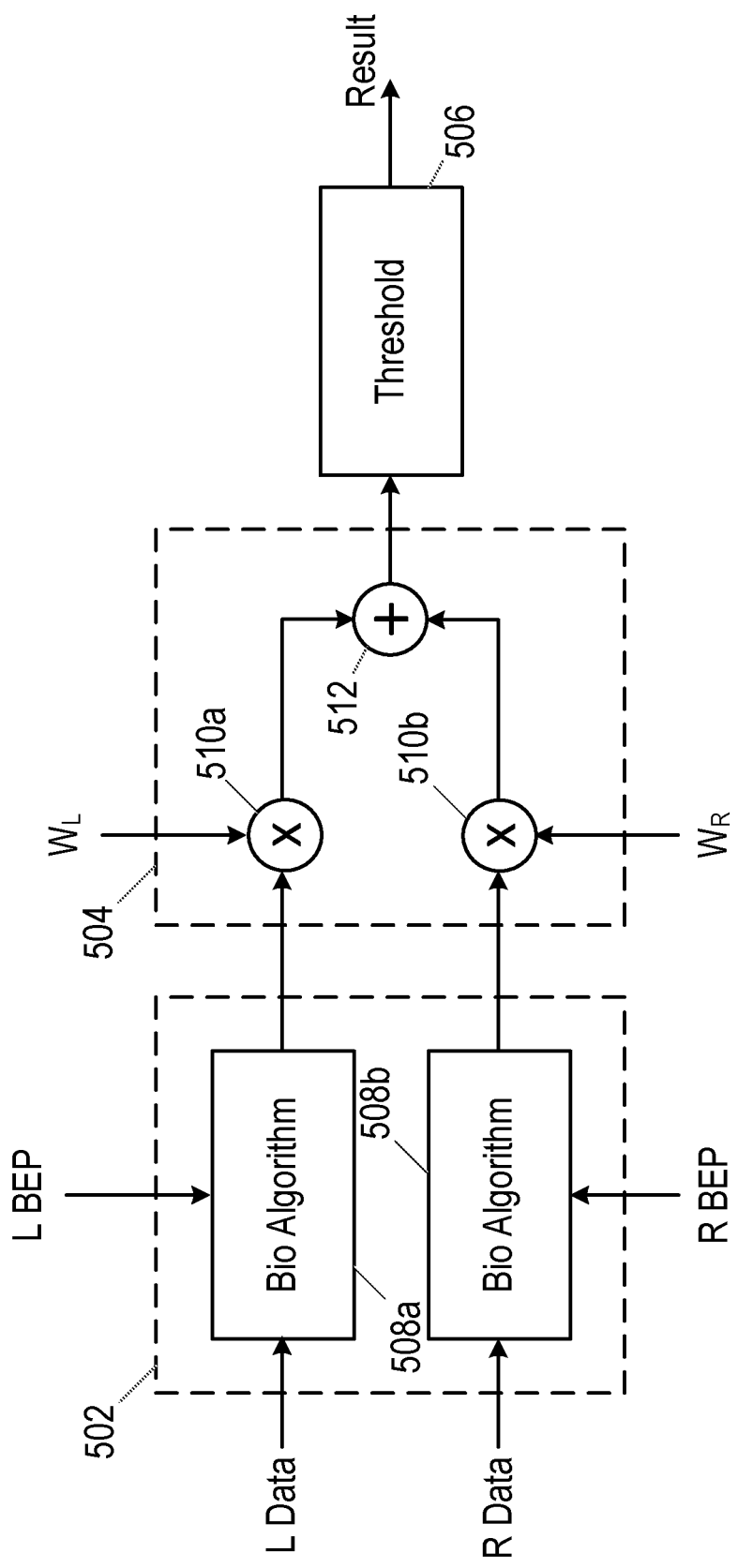
FIG. 8 is a schematic diagram of a biometric processor according to embodiments of the disclosure.

FIG. 8 is a schematic diagram showing a mechanism for performing such an authentication process according to embodiments of the disclosure. The mechanism may be implemented within the biometric module 414 described above with respect to FIG. 7.

The mechanism comprises a processing module 502, a fusion module 504 and a threshold module 506. The processing module 502 implements biometric algorithms 508a, 508b (collectively 508) which compare features extracted from the signals reflected from the ears of the user with stored earprints to generate corresponding biometric scores which are indicative of the similarity between the input data and the stored earprints. Thus a first biometric algorithm 508a involves a comparison between the features extracted from the signal reflected from the left ear of the user with the earprint 416a for the left ear (left biometric earprint, or L BEP); a second biometric algorithm 508b involves a comparison between the features extracted from the signal reflected from the right ear of the user with the earprint 416b for the right ear (right biometric earprint, or R BEP). Those skilled in the art will appreciate that the processing module 502 may alternatively implement a single biometric algorithm which is multiplexed between processing for the left and right ears.

Separate biometric scores are determined for each ear based on the comparisons. In some embodiments, the biometric scores may additionally be obtained based on a comparison between the features extracted from the reflected signals and one or more profiles acquired from one or more cohorts of other users.

The biometric scores are output to the fusion module 504, which, in some embodiments, multiplies each biometric score by its respective weight. In the illustrated embodiment, the fusion module 504 comprises a first multiplication node 510a for multiplying the biometric score for the left ear by the weight $w_L$ for the left ear, and a second multiplication node 510b for multiplying the biometric score for the right ear by the weight $w_R$ for the right ear. The weighted biometric score are then combined (e.g., added) in an adding node 512 to generate an overall biometric score. Note that the ear biometric scores described herein may be combined with one or more further biometric scores (such as voice, fingerprint, iris biometrics, etc) to generate the overall biometric score.

In alternative embodiments, the fusion module 504 may be configured to apply weights to the biometric scores and to combine any such weighted biometric scores differently. For example, weights may be applied to the biometric scores for the left and right ears in a linear function (such as a linear affine function as described above). Alternatively or additionally, weights may be applied as part of a polynomial transform to the biometric scores separately and in combination, e.g., $$\sum_{i=0}^{p}\sum_{j=0}^{q}\alpha_{ij}S_L^i S_R^j$$

where p and q denote degrees of the polynomial in the first and second biometric scores respectively, and where $S_L$ and $S_R$ are the first and second biometric scores respectively. These weighted (transformed) biometric scores may be combined by addition to generate the overall biometric score (as mentioned above), or in a non-linear function such as a sigmoid (logistic) function, a double sigmoid function, a tanh function, etc.

The overall biometric score is output to the threshold module 506, which compares it to one or more thresholds to generate a biometric result. The biometric result may be provided to the control module 410 or further action.

In a simple embodiment, the threshold module 506 may compare the overall biometric score to a single, first threshold which is set to determine whether the biometric data corresponds to the authorised user (i.e. corresponding to the stored earprints 416) or not. In this case the biometric result may correspond to an indication that the user is authorised or not. One or more additional thresholds may be used to determine whether the biometric data is within a defined range of meeting the first threshold. In this case, the biometric result may be used to provide feedback to the user to reposition the apparatus 400 and particularly the loudspeakers 406. In yet further embodiments, the threshold may be set at a lower level to identify whether the biometric data corresponds to an ear (i.e. any ear) or not. In this way, the biometric module 414 may be used as an in-ear detection function. For example, in-ear detection (and conversely out-of-ear detection) may be used to move the apparatus 400 between low-power and high-power operating states, or to perform one or more predefined actions (such as starting or stopping playback, for example).

Thus embodiments of the disclosure provide methods, apparatus and computer-readable media for performing biometric processes based on biometric data acquired from the left and right ears of a user. The scores for the left and right ears are fused in a weighted sum, with the weights being configured to emphasize the score for the ear which is more discriminative with respect to one or more cohorts of users.

Figure 9:
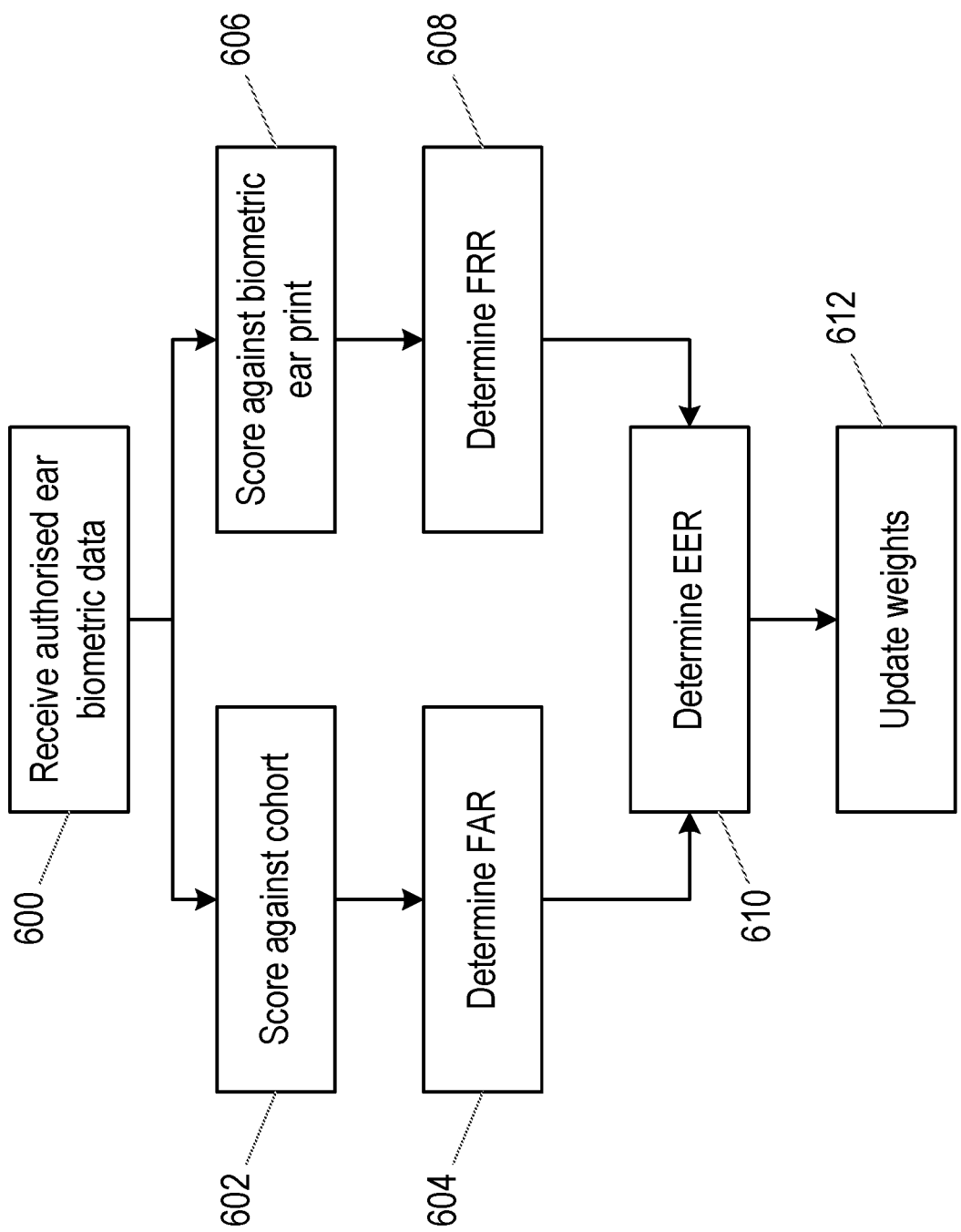
FIG. 9 is a flowchart of a method of updating weights according to embodiments of the disclosure.

FIG. 9 is a flowchart of a method of calculating the weights $w_L$ and $w_R$. The method is described with respect to one ear, but may be repeated for a second ear.

The method may be performed by the biometric module 414 described above with respect to FIG. 7, for example. As will be clear from the following description, the method may be performed during enrolment (i.e., where an authorised user generates stored profiles or "earprints" for future use in authentication), or during ordinary use of the electronic apparatus 400. In some embodiments, the method is performed both during enrolment and subsequently during ordinary use of the electronic apparatus 400 (i.e., in a mode of operation other than enrolment, such as audio playback, during a phone call, etc). That is, first values for the weights $w_L$ and $w_R$ may be obtained during enrolment, with those values subsequently being updated based on new data acquired during ordinary use of the apparatus. In other embodiments, first values for the coefficients $\alpha_0, \alpha_R, \alpha_L$, (or $a_{ij}$) may be obtained during training, updated during enrolment, and subsequently updated further based on new data acquired during ordinary use of the apparatus.

In step 600, ear biometric data is obtained for an authorised user. As noted above, the ear biometric data may comprise one or more features extracted from an acoustic signal which is reflected off an ear of the user. The features extracted from the signals may comprise one or more of: one or more resonant frequencies of the respective ear; one or more cepstrum coefficients (such as mel frequency cepstrum coefficients); the frequency response of the ear at one or more predetermined frequencies, or across one or more ranges of frequencies.

It will be noted here that the ear biometric data is for a user who is known or assumed to be authorised. For example, the user may have already been authenticated as an authorised user, through biometric authentication (whether ear biometrics or some other modality such as voice, fingerprint, iris, etc), responding to a request for a security password or passphrase, etc. This may particularly be the case where the method of FIG. 9 is performed during normal operation of the electronic apparatus, or when ear biometric enrolment is performed subsequent to some other authentication process. Alternatively, the process may be performed on initial set-up of the electronic apparatus, when no authorised user is yet established for the apparatus.

The received ear biometric data is used to obtain a false acceptance rate (FAR) and a false rejection rate (FRR). These parameters may be obtained in parallel (as illustrated) or sequentially.

Thus, in step 602, the received ear biometric data is compared against one or more cohorts of users (not including the authorised user) to generate one or more corresponding biometric scores indicative of the similarity (e.g., through a function such as the cosine similarity) between the received ear biometric data and the one or more cohorts of users. Multiple scores may be obtained based on multiple sets of ear biometric data for the authorised user, and/or by rotating the data values to generate new data.

The scores obtained in step 602 are used to form a set of non-target scores, i.e. scores which are indicative of non-correspondence between input ear biometric data and the ear biometric data of the authorised user.

In step 604, the FAR is obtained based on the non-target scores obtained in step 602, and in particular the variation of the FAR is obtained for a range of threshold values. Thus the FAR is calculated based on that proportion of the non-target scores which are greater than the threshold for a range of threshold values. These scores would be falsely accepted by the biometric module.

In step 606, the received ear biometric data is compared against a stored biometric earprint for the particular ear. If no stored biometric earprint is yet available, the first set of ear biometric data for the authorised user is used as the biometric earprint, and subsequent sets of ear biometric data are compared to the first. Based on the comparison, one or more corresponding biometric scores are generated indicative of the similarity (e.g., through a function such as the cosine similarity) between the received ear biometric data and the stored earprint. The scores obtained in step 606 are used to form a set of target scores, i.e. scores which are indicative of correspondence between input ear biometric data and the ear biometric data of the authorised user.

In step 608, the FRR is obtained based on the target scores obtained in step 606, and in particular the variation of the FRR is obtained for a range of threshold values. Thus the FRR is calculated based on that proportion of the target scores which are less than the threshold for a range of threshold values. These scores would be falsely rejected by the biometric module.

In step 610, the variations of the FAR and FRR are utilized to determine the equal error rate (EER): the error rate for the threshold value at which the FAR and FRR are equal to each other. As noted above, the EER is an indicator for the discriminative ability of a biometric process or biometric data. In the present context, the EER is indicative of the discriminative ability of the stored earprint.

In step 612, the weights for the left and right ears, $w_L$ and $w_R$, are determined or updated based on the EER. As noted above, in one embodiment, the weights are calculated according to the following equations:

$$w_L = \frac{EER_R}{EER_L + EER_R}$$

$$w_R = \frac{EER_L}{EER_L + EER_R}$$

where $EER_L$ is the EER associated with the left ear, and $EER_R$ is the EER associated with the right ear.

Here it will be recalled that the lower the EER, the more discriminative the biometric data. Thus in this example, the weights for each ear are configured inversely proportional to the EER for the respective ear.

In another example, the weights may be configured so as to optimize the false rejection rate or the false acceptance rate. Here the weights may be configured proportionally to the respective false rejection rate or false acceptance rate. In one example, which depends on the false rejection rate, the weights may be configured as follows:

$$w_L = \frac{FRR_L}{FRR_L + FRR_R}$$

$$w_R = \frac{FRR_R}{FRR_L + FRR_R}$$

where $FRR_L$ is the FRR associated with the left ear, and $FRR_R$ is the FRR associated with the right ear. In this embodiment, therefore, the EER may not be calculated, and the FAR may not be calculated.

In another example, which depends on the false acceptance rate, the weights may be configured as follows:

$$w_L = \frac{FAR_L}{FAR_L + FAR_R}$$

$$w_R = \frac{FAR_R}{FAR_L + FAR_R}$$

where $FAR_L$ is the FAR associated with the left ear, and $FAR_R$ is the FAR associated with the right ear. In this embodiment, therefore, the EER may not be calculated, and the FRR may not be calculated.

In other embodiments, as noted above, the coefficients $\alpha_0, \alpha_R, \alpha_L$ of a linear affine transform $g(S_R, S_L) = \alpha_0 + \alpha_R S_R + \alpha_L S_L$ are constants whose values are determined by minimizing a cost function $J(h, \alpha_0, \alpha_R, \alpha_L)$ over a training set of example right and left ear biometric score pairs $(S_R^{(i)}, S_L^{(i)})$. The coefficients $\alpha_0, \alpha_R, \alpha_L$ may also be termed weights herein. This training set may be derived from measurements of the left and right acoustic ear biometric features, obtained from multiple subjects, which have been scored by left and right ear biometric processors. An example of a cost function $J(h, \alpha_0, \alpha_R, \alpha_L)$ whose minimization optimizes the values of the coefficients $\alpha_0, \alpha_R, \alpha_L$ is the log-likelihood cost function $$J(h, \alpha_0, \alpha_R, \alpha_L) = -\frac{1}{m}\sum_{i=1}^{m}\left[y^{(i)}\log(h(S_R^{(i)}, S_L^{(i)})) + (1-y^{(i)})(1-\log(h(S_R^{(i)}, S_L^{(i)})))\right] + \beta(\alpha_R^2 + \alpha_L^2) \quad (3)$$

Here m is the number of training examples, p≥0 is a constant regularization parameter (which may be adjusted to improve the speed or robustness of the optimization procedure), and $y^{(i)}=1$ if the ith training example belongs to the target (authorized user) class and 0 otherwise. Those skilled in the art will appreciate that alternative cost functions may be used without departing from the scope of the claims appended hereto.

Gradient descent is one example of an efficient iterative procedure which will minimize a cost function $j(h, \alpha_0, \alpha_R, \alpha_L)$ as in (3) to produce optimal values of the coefficients $\alpha_0, \alpha_R, \alpha_L$. Those skilled in the art will appreciate that other optimization procedures may also be used with similar effectiveness.

As noted above, in some embodiments the weights are first obtained during enrolment and subsequently updated based on data acquired during ordinary use of the apparatus. In such embodiments, the new weight values may be calculated as combinations of the values obtained during enrolment (or otherwise those values previously used), and values obtained by following the method of FIG. 9 based on new ear biometric data. For example, the new weight values may correspond to averages of the previous or "old" values and the values obtained based on new ear biometric data. Such averages may themselves be weighted, for example such that the new weight values are predominantly based on the old values, such that the values do not change rapidly and become vulnerable to attack by unauthorised users. Alternatively, the amount by which a weight value is permitted to change may be limited so as to prevent rapid change in their values.

Embodiments may be implemented in an electronic, portable and/or battery powered host device such as a smartphone, an audio player, a mobile or cellular phone, or a handset. Embodiments may be implemented on one or more integrated circuits provided within such a host device. Embodiments may be implemented in a personal audio device configurable to provide audio playback to a single person, such as a smartphone, a mobile or cellular phone, headphones, earphones, etc., see FIG. 1a to 1e. Again, embodiments may be implemented on one or more integrated circuits provided within such a personal audio device. In yet further alternatives, embodiments may be implemented in a combination of a host device and a personal audio device. For example, embodiments may be implemented in one or more integrated circuits provided within the personal audio device, and one or more integrated circuits provided within the host device.

It should be understood—especially by those having ordinary skill in the art with the benefit of this disclosure—that the various operations described herein, particularly in connection with the figures, may be implemented by other circuitry or other hardware components. The order in which each operation of a given method is performed may be changed, and various elements of the systems illustrated herein may be added, reordered, combined, omitted, modified, etc. It is intended that this disclosure embrace all such modifications and changes and, accordingly, the above description should be regarded in an illustrative rather than a restrictive sense.

Similarly, although this disclosure makes reference to specific embodiments, certain modifications and changes can be made to those embodiments without departing from the scope and coverage of this disclosure. Moreover, any benefits, advantages, or solutions to problems that are described herein with regard to specific embodiments are not intended to be construed as a critical, required, or essential feature or element.

Further embodiments likewise, with the benefit of this disclosure, will be apparent to those having ordinary skill in the art, and such embodiments should be deemed as being encompassed herein.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A biometric processor, comprising:
   one or more inputs configured to receive first ear biometric data acquired in respect of a first ear of a user and second ear biometric data acquired in respect of a second ear of the user;
   a processing module configured to perform one or more biometric algorithms on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores;
   a fusion module configured to apply first and second weights to the respective first and second biometric scores to obtain first and second weighted biometric scores, and to combine at least the first and second weighted biometric scores to generate an overall biometric score, wherein the first and second weights are different to each other; and
   wherein a biometric result is based on the overall biometric score;

wherein the first weight varies inversely proportionally with the equal error rate associated with the first stored ear biometric template.

2. The biometric processor according to claim 1, wherein the first stored ear biometric template is more discriminative than the second stored ear biometric template, and wherein the first and second weights are configured such that the first weight is greater than the second weight.

3. The biometric processor according to claim 1, wherein the first weight varies as a function of one or more of: a false rejection rate associated with the first stored ear biometric template; and a false acceptance rate associated with the first stored ear biometric template.

4. The biometric processor according to claim 3, wherein the first weight varies proportionally with the false rejection rate or the false acceptance rate associated with the first stored ear biometric template.

5. The biometric processor according to claim 4, wherein the first weight is calculated according to the following equation:

$$w_1 = \frac{FRR_1}{FRR_1 + FRR_2},$$

where $w_1$ is the first weight, $FRR_1$ is the false rejection rate associated with the first stored ear biometric template, and $FRR_2$ is a false rejection rate associated with the second stored ear biometric template, or wherein the first weight is calculated according to the following equation:

$$w_1 = \frac{FAR_1}{FAR_1 + FAR_2},$$

where $w_1$ is the first weight, $FAR_1$ is the false acceptance rate associated with the first stored ear biometric template, and $FAR_2$ is a false acceptance rate associated with the second stored ear biometric template.

6. The biometric processor according to claim 1, wherein the first weight is calculated according to the following equation:

$$w_1 = \frac{EER_2}{EER_1 + EER_2},$$

where $w_1$ is the first weight, $EER_1$ is the equal error rate associated with the first stored ear biometric template, and $EER_2$ is the equal error rate associated with the second stored ear biometric template.

7. The biometric processor according to claim 1, wherein the first and second weights are calculated based on biometric data acquired during enrolment of the authorised user.

8. The biometric processor according to claim 7, wherein the first and second weights are updated, subsequent to enrolment of the authorised user, based on biometric data acquired in a mode of operation other than enrolment.

9. The biometric processor according to claim 7, wherein the first and second weights are further calculated based on a training set of biometric scores obtained from a cohort of subjects.

10. The biometric processor according to claim 9, wherein the first and second weights are calculated by minimizing a cost function based on the training set of biometric scores and the biometric data acquired during enrolment of the authorised user.

11. The biometric processor according to claim 1, wherein the first and second weighted biometric scores are combined in a non-linear function, the non-linear function having a slope which varies as a function of relative discriminative values of the first and second biometric scores.

12. The biometric processor according to claim 1, wherein the first ear biometric data and the second ear biometric data comprise acoustic data.

13. The biometric processor according to claim 12, wherein the first ear biometric data comprises an acoustic response of the first ear of the user to a first acoustic stimulus, and wherein the second ear biometric data comprises an acoustic response of the second ear of the user to a second acoustic stimulus.

14. The biometric processor according to claim 12, wherein the first ear biometric data comprises one or more first features extracted from an acoustic response of the first ear of the user to a first acoustic stimulus, and wherein the second ear biometric data comprises one or more second features extracted from an acoustic response of the second ear of the user to a second acoustic stimulus.

15. The biometric processor according to claim 14, wherein the one or more first features and the one or more second features each comprise one or more of: one or more resonant frequencies of the respective acoustic responses; cepstral coefficients of the respective acoustic responses; and a transfer function between the first and second acoustic stimuli and the respective acoustic responses.

16. The biometric processor according to claim 12, wherein the first ear biometric data comprises an otoacoustic emission from the first ear of the user, and wherein the second ear biometric data comprises an otoacoustic emission from the second ear of the user.

17. The biometric processor according to claim 1, further comprising a threshold module configured to compare the overall biometric score to one or more thresholds in order to generate the biometric result.

18. A method of performing a biometric process, the method comprising:
obtaining first ear biometric data acquired in respect of a first ear of a user and second ear biometric data acquired in respect of a second ear of the user;
performing one or more biometric algorithms on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores;
applying first and second weights to the respective first and second biometric scores to obtain first and second weighted biometric scores, and combining at least the first and second weighted biometric scores to generate an overall biometric score, wherein the first and second weights are different to each other; and
generating a biometric result based on the overall biometric score;
wherein the first weight varies inversely proportionally with the equal error rate associated with the first stored ear biometric template.

19. An electronic apparatus comprising processing circuitry and a non-transitory machine-readable medium storing instructions which, when executed by the processing circuitry, cause the processing circuitry to:

obtain first ear biometric data acquired in respect of a first ear of a user and second ear biometric data acquired in respect of a second ear of the user;

perform one or more biometric algorithms on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores;

apply first and second weights to the respective first and second biometric scores to obtain first and second weighted biometric scores, and combine at least the first and second weighted biometric scores to generate an overall biometric score, wherein the first and second weights are different to each other; and generate a biometric result based on the overall biometric score;

wherein the first weight varies inversely proportionally with the equal error rate associated with the first stored ear biometric template.

20. A biometric processor, comprising:

one or more inputs configured to receive first ear biometric data acquired in respect of a first ear of a user and second ear biometric data acquired in respect of a second ear of the user;

a processing module configured to perform one or more biometric algorithms on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores;

a fusion module configured to apply first and second weights to the respective first and second biometric scores to obtain first and second weighted biometric scores, and to combine at least the first and second weighted biometric scores to generate an overall biometric score, wherein the first and second weights are different to each other; and wherein a biometric result is based on the overall biometric score, wherein the first weight varies proportionally with a false rejection rate or a false acceptance rate associated with the first stored ear biometric template.

21. A biometric processor, comprising:

one or more inputs configured to receive first ear biometric data acquired in respect of a first ear of a user and second ear biometric data acquired in respect of a second ear of the user;

a processing module configured to perform one or more biometric algorithms on the first ear biometric data and the second ear biometric data, based on a comparison of the first ear biometric data to a first stored ear biometric template for an authorised user and a comparison of the second ear biometric data to a second stored ear biometric template for the authorised user, to obtain respective first and second biometric scores;

a fusion module configured to apply first and second weights to the respective first and second biometric scores to obtain first and second weighted biometric scores, and to combine at least the first and second weighted biometric scores to generate an overall biometric score, wherein the first and second weights are different to each other; and wherein a biometric result is based on the overall biometric score, wherein the first and second weights are calculated based on biometric data acquired during enrolment of the authorised user and a training set of biometric scores obtained from a cohort of subjects.

* * * * *